United States Patent [19]

Rosenberg et al.

[11] Patent Number: 4,998,070

[45] Date of Patent: Mar. 5, 1991

[54] METHOD AND APPARATUS FOR TESTING A DIELECTRIC COATING

[75] Inventors: Jerome C. Rosenberg, Bellevue; Robert S. Dobrowski, Maple Valley, both of Wash.

[73] Assignee: The Boeing Company, Seattle, Wash.

[21] Appl. No.: 517,410

[22] Filed: Apr. 27, 1990

Related U.S. Application Data

[63] Continuation of Ser. No. 266,085, Nov. 2, 1988, abandoned.

[51] Int. Cl.⁵ ...................... G01R 31/02; G01R 31/12
[52] U.S. Cl. .................................... 324/557; 324/544; 324/559
[58] Field of Search ............... 324/509, 513, 515, 536, 324/541, 544, 551, 557-559, 72.5; 340/647

[56] References Cited

U.S. PATENT DOCUMENTS

| | | | |
|---|---|---|---|
| 1,561,483 | 11/1925 | Pickard | 324/554 |
| 2,304,513 | 12/1942 | Stearns | 324/557 |
| 2,329,098 | 9/1943 | Browning et al. | 324/553 X |
| 2,332,182 | 10/1943 | Stearns | 324/559 |
| 2,478,414 | 8/1949 | Michal | 324/555 |
| 2,716,216 | 8/1955 | Schwenzfeier | 324/555 X |
| 2,866,156 | 12/1958 | Lane | 324/559 |
| 2,885,636 | 5/1959 | Rasor | 324/557 |
| 2,900,597 | 8/1959 | Gooding | 324/515 X |
| 3,277,364 | 10/1966 | Abrahamson | 340/647 X |
| 3,649,954 | 3/1972 | Kurtz | 324/72.5 X |
| 4,724,376 | 2/1988 | Slough et al. | 324/557 X |

FOREIGN PATENT DOCUMENTS 2752957 5/1979 Fed. Rep. of Germany ...... 324/557

Primary Examiner—Reinhard J. Eisenzopf
Assistant Examiner—Jack B. Harvey
Attorney, Agent, or Firm—Seed and Berry

[57] ABSTRACT

A method and apparatus for testing the integrity of the dielectric coating on an elongated member. The apparatus includes a pair of opposing, conducting surfaces that can be biased against the dielectric surface, a source of high voltge that can be switchably imposed on the conducting surfaces, a ground for completing an electrical circuit between the elongated member and the source of high voltage, and an electrical circuit for detecting the passage of current through the electrical ground. A first visible indicator on the apparatus shows when the high voltage is applied to the conducting surfaces and a second visible indicator shows when a current is detected through the electrical ground. This apparatus allows the conducting surfaces to be moved longitudinally along the elongated member to test the dielectric integrity of virtually the entire dielectric surface in a single pass. If small gaps exist between the two conducting surfaces in a longitudinal direction, the apparatus can be rotated through an angle about the longitudinal direction and the apparatus passed along the elongated member a second time.

8 Claims, 2 Drawing Sheets

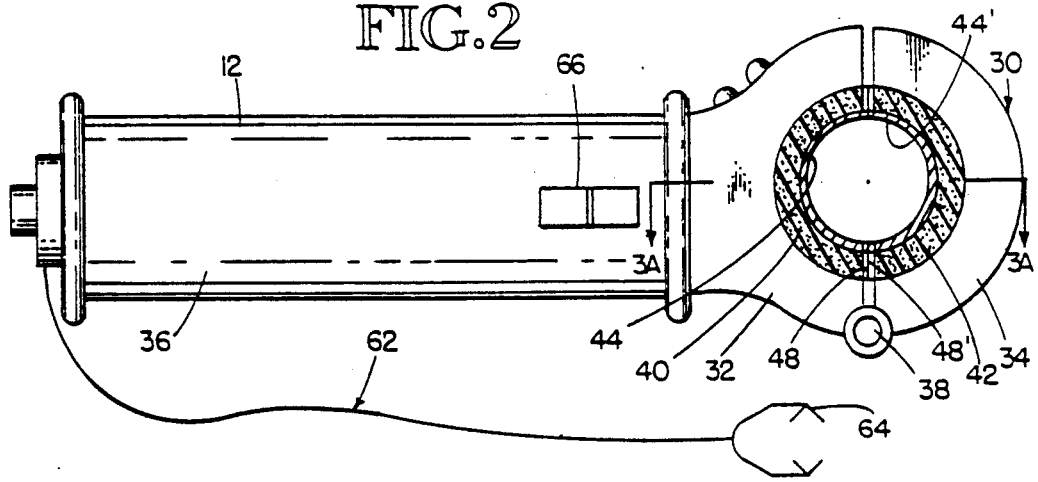
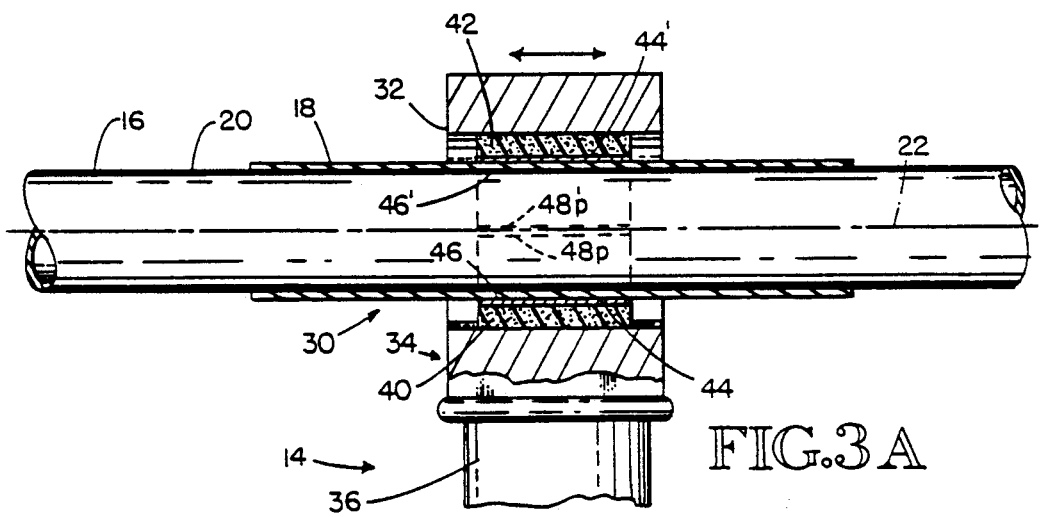
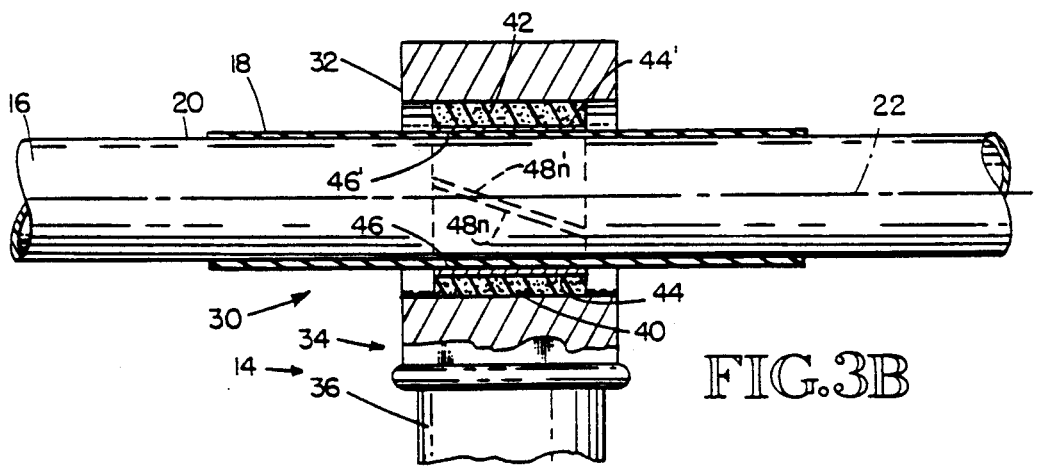

METHOD AND APPARATUS FOR TESTING A DIELECTRIC COATING

GOVERNMENT RIGHTS

The government has certain rights in this invention.

CROSS-REFERENCE TO RELATED APPLICATION

This application is a continuation of United States application Ser. No. 07/266,085 filed Nov. 2, 1988, now abandoned.

TECHNICAL FIELD

The present invention relates to a method and apparatus for testing a dielectric fitting and, more particularly, a method and apparatus for imposing a voltage across a dielectric coating and for measuring any resulting current through the dielectric coating.

BACKGROUND OF THE INVENTION

It is typically necessary to run metallic lines, such as tubing carrying hydraulic fluid or fuel through aircraft structures. In many instances, such lines necessarily closely approach fuel tanks or other sources of ignitable materials. In order to prevent an electrical arc from occurring due to a lightning strike on the aircraft structure, possibly igniting these materials, it is necessary to apply a dielectric insulation to the outer surface of the metallic lines.

This is a particular problem in aircraft structures made from low-conductivity composite materials. A high current surge imposed in a composite material aircraft structure by a lightning strike will cause a high voltage to be generated between the low-conductivity structure and the metallic tubing. This generated high voltage is particularly hazardous where the tubing is supported by clamps. The dielectric insulation presently used is one or more layers of MIL-I-23053/8 (Kynar) heat shrink tubing or some form of Kapton film.

One difficulty with the use of such insulating material is that it is difficult to check the dielectric strength of the material after it has been installed on the tubing. This is particularly so after the tubing has been placed in the aircraft structure. Since the dielectric material is fragile, it can easily and unknowingly be damaged during assembly or subsequent servicing, with a resultant loss of its dielectric strength. A lightning strike could then cause a spark near a fuel tank and result in the loss of the aircraft.

Various apparatus have been proposed in the past for testing dielectric coating on tubing and the like. For example, Saw, in U.S. Pat. No. 2,920,270, discloses a high-voltage insulation tester for detecting flaws in coated pipes. Saw's invention, which is intended for use with pipes which have been buried in the ground, incorporates a test instrument having a grounding lead that can be connected to a spike driven into the ground and a high-voltage lead with a "bracelet" made from a helical metal spring. The metal spring is stretched around the outer surface of the pipe whose coating is to be tested and the voltage applied. The test instrument detects any current passing through an external leakage path which includes a break in the dielectric coating formed around the pipe. The bracelet can slide along the pipe to test the dielectric coating. However, since the spring bracelet only touches the coated pipe at those discrete points where the helix of the spring is closest to the pipe, the apparatus disclosed by Saw can provide only a rough test of the integrity of the coating on the pipe. For example, breaks in the dielectric coating which are smaller than the separation between adjacent wraps of the spring bracelet may not be detected by the apparatus disclosed in Saw, even if the bracelet makes multiple passes along the pipe.

Mantilla, in U.S. Pat. No. 2,237,187, discloses a trouble detector which checks for electrical faults by penetrating the insulation around electrical conductors. The apparatus disclosed by Mantilla therefore destroys the integrity of the dielectric coating at discrete points and, accordingly, is unsuitable for testing the integrity of the dielectric coating formed around a hydraulic fluid or fuel line. In addition, the apparatus disclosed by Mantilla is incapable of being moved along the length of the tubing while performing its testing function.

Kamper, in U.S. Pat. No. 2,229,927, discloses an electrical tester for checking automotive electrical systems. Kamper's apparatus consists of a hand-held tool having electrical connectors and indicator lights. Kamper's tool makes probing contact with electrical conductors at single points. Once a connection has been made between the tool and the electrical conductor, the tool cannot be moved along the conductor without breaking the connection.

Further, Wiseman et al., in U.S. Pat. No. 3,810,007, disclose a "holiday" detector and coating resistivity checker which incorporates a ring-shaped probe employing a sponge which is saturated with a suitable electrolyte. The probe is slipped over a pipe whose coating is to be tested and is then longitudinally moved along the pipe to test for breaks in the dielectric coating. Wiseman et al. disclose a second form of a probe having a rectangular contact surface attached to a handle for use in checking portions of nonconducting coatings on large vessels or large-diameter pipes. Wiseman et al. do not disclose a probe which can simultaneously test substantially the full circumference of a pipe which does not have at least one end accessible.

Accordingly, it is desirable to have a method and apparatus for testing a dielectric coating which can simply and efficiently test the integrity of a dielectric coating formed on the outer surface of an elongated member which does not necessarily have at least one end accessible.

DISCLOSURE OF THE INVENTION

It is an object of the present invention to provide means for simultaneously testing the dielectric integrity of substantially the entire perimeter of the dielectric coating on an elongated member.

It is another object of the present invention to provide a method for simultaneously testing the dielectric integrity of substantially the entire perimeter of the dielectric coating on an elongated member.

It is a further object of the present invention to provide an apparatus for testing the integrity of a dielectric coating on an elongated member whose ends are inaccessible.

Yet another object of the present invention to provide an apparatus for testing the integrity of a dielectric coating formed on the outer surface of an elongated member, regardless of changes in the external shape of the elongated member.

Still another object of the present invention is to provide a method and apparatus for testing the integrity of a dielectric coating on an elongated member in a convenient manner.

According to one aspect, the invention is an apparatus for testing the integrity of a dielectric coating on an outer surface of an elongated electrolyte conductive member, the outer surface having a perimeter around the elongated member. The apparatus comprises first means for forming an electrically conductive path to the dielectric coating and means for forcing said first means against the dielectric coating along a substantially closed curve around the perimeter of the outer surface. The apparatus further comprises second means for making electrical connection to the elongated member, and third means for making an electrical connection to the first means.

In another aspect, the apparatus of the invention comprises first means for forming an electrically conductive path to the dielectric coating, the path forming a substantially closed curve around the perimeter of the outer surface and means for forcing the first means against the dielectric coating along a substantially closed curve around the perimeter of the outer surface. In addition, the apparatus comprises second means for making electrical connection to the elongated member and first indicator means for providing a first visual indication in response to a first indication signal. The apparatus further comprises second indicator means for providing a second visual indication in response to a second indication signal, and an electric circuit connected between the first means and the second means for imposing a high voltage between the first means and the second means, for detecting the passage of electrical current through the dielectric coating in response to the high voltage, and for producing the first indication signal.

In yet another aspect of the present invention is a method for testing the integrity of a dielectric coating on the outer surface of an elongated, electrically conductive member. The method comprises the steps of (a) forming an electrically conductive path to the dielectric coating, (b) forcing the electrically conductive path against the dielectric coating along a substantially closed curve around the perimeter of the outer surface, (c) making an electrical connection to the elongated member, and (d) making an electrical connection to the electrically conductive path.

BRIEF DESCRIPTION OF THE DRAWINGS

FIG. 2 is a diagram of an embodiment of the hand tool of the present invention.

FIG. 3A is a cross-sectional view of a first embodiment of the head of the hand tool of the present invention, taken along lines 3—3' in FIG. 2.

FIG. 3B is a cross-sectional view of a second embodiment of the head of the hand tool of the present invention, taken along lines 3—3' in FIG. 2.

DETAILED DESCRIPTION OF THE INVENTION

Figure 1:
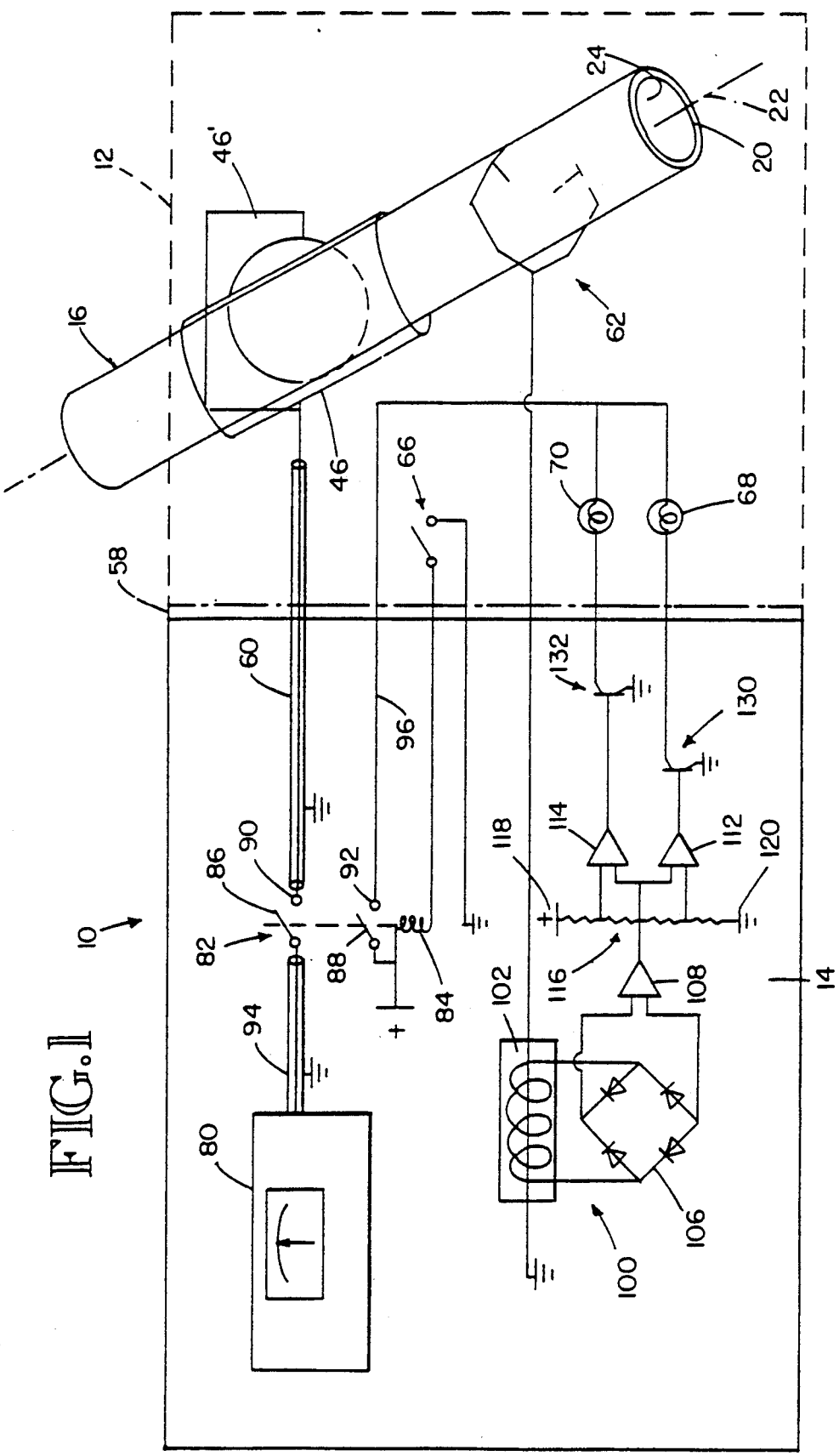
FIG. 1 is a schematic diagram of the electrical circuitry of the present invention.

Referring to FIG. 1, the apparatus 10 of the present invention includes a hand tool 12 connected to a high-voltage dielectric test set 14. The hand tool 12 is designed to engage a conductive elongated member 16 having a dielectric coating 18 over its outer surface 20. The elongated member 16 has an axis 22.

The hand tool 12 can be passed along the length of the elongated member 16, simultaneously testing the dielectric integrity of substantially all of the dielectric coating 18 formed on a circumference or perimeter of the outer surface 20. Any remaining untested portion of the dielectric coating 18 can be tested on a subsequent pass along the elongated member 16, for example, in the opposite direction.

The hand tool 12 comprises a head 30 (see FIGS. 2, 3A, and 3B) made in the form of a split ring having a first portion 32 and a second portion 34. The first portion 32 of the split ring is attached to a handle 36 of the hand tool. The second portion 34 of the split ring can be pivoted with respect to the first portion of the split ring around a pivot 38. The pivot 38 can incorporate a spring (not shown) to bias the second portion into a closed configuration with the first portion 32. The inner surfaces of the first and second portions 32 and 34 can be covered by semicircular spongy inserts 40 and 42, respectively, forming a cylindrical inner surface 44 having two subsurfaces, 44 and 44'. The inner surfaces 44 and 44' are respectively covered with conducting surfaces 46 and 46'. In operation, the head 30 of the hand tool 12 forces the conducting surfaces 46 and 46' against the dielectric coating 18 applied to the outer surface 20 of the elongated member 16. The spongy inserts 40 and 42 can make minor adjustments in shape and size to account for variations in the shape and size of the elongated member 16.

By means of the handle 36, the head 30 of hand tool 12 can be passed along the length of the elongated member 15 in the direction of the axis 22, simultaneously checking all portions of the dielectric coating 18 on a circumference or perimeter, except possibly for small gaps between the two cylindrical inner surfaces 44 and 44'. When using the embodiment of the head 30 shown in FIG. 3A, two small strips of the dielectric coating 18 which pass between the edges 48p and 48p' of the spongy inserts 40 and 42 and the conducting surfaces 46 and 46' may be untested. The integrity of the dielectric coating 18 in these remaining small strips can be subsequently tested by rotating the handle 36 about the direction of elongation of the elongated member 16 so that the strips will be covered by the conducting surfaces 46 and 46' in the second pass of the hand tool 12.

Alternatively, if desired, the conducting surfaces 46 and 46', and their supporting spongy inserts 40 and 42 can be cut on an angle so that their meeting edges 48 meet along a surface that is not parallel to the direction of the elongated member 16. This is shown in "FIG. 3B, in which the edges 48n and 48n' are not parallel to the axis 22. In this second embodiment, the head 30 need only be passed along the elongated member 16 once to test the entire dielectric coating 18.

Referring again to the schematic diagram of FIG. 1, the hand tool 12 includes electrical circuitry which can be connected to the dielectric test set 14 through a conventional connector 58. The hand tool 12 includes the conducting surfaces 46 and 46' which are electrically connected together through an electrical conductor passing through the pivot 38. The conducting surfaces 46 and 46' receive a high test voltage from the dielectric test set 14 through a shielded cable 60 which passes between the hand tool 12 and the dielectric test set 14. The shielded cable 60 can be grounded at the end of the cable 60 that is connected to the dielectric test set 14.

The hand tool 12 also includes a ground clamp 62 which can be connected to ground through the connector 58 in the dielectric test set 14. The ground clamp 62 can include an electrical fitting 64 which can be clamped to the elongated member 16. In accordance with this configuration, the existence of any breaks in the integrity of the dielectric coating 18 will cause an electrical current to pass through the ground clamp 62 as a result of the high voltage imposed by the conducting surfaces 46 and 46'.

The hand tool 12 also incorporates an on-off switch 66, and two visible indicators 68 and 70. The on-off switch 66 and the visible indicators 68 and 70 are connected to the dielectric test set 14 through the connector 58.

The dielectric test set 14 includes a high-voltage power supply 80 capable of producing, for example, 30 kilovolts. The dielectric test set 14 also includes a double-pole, double-throw relay switch 82. The relay switch 82 can be activated and deactivated by the on-off switch 66, to which it is connected through connector 58. When the on-off switch 66 is placed in its on position, the relay coil 84 of the relay switch 82 is energized by the passage of electrical current therethrough. This causes the two throws 86 and 88 to be closed against their respective poles 90 and 92. The high voltage imposed by the high-voltage power supply 80 and path to the throw 86, through the grounded shielded cable 94, is imposed on the conducting surfaces 46 and 46' through the grounded shielded cable 60. Simultaneously, a supply voltage is supplied to line 96 through throw 88 and pole 92. This supply voltage is passed, through the connector 58, to each of the visible indicators 68 and 70.

The dielectric test set 14 also includes a current-detection circuit 100, which includes a coil 102 formed around the lead 104 which is attached to the ground clamp 62 through the connector 58. Any current passing through the lead 104 generates a voltage across the coil 102 which is detected by the conventional rectifying bridge 106. The output of the rectifying bridge 106 is passed through a differential amplifier 108 to the balanced circuit 110 which includes differential amplifiers 112 and 114, as well as biasing resistor network 116. The biasing resistor network is connected between a supply voltage 118 and a ground 120. Differential amplifiers 112 and 114 are respectively connected to the bases of transistors 130 and 132, whose emitters are grounded and whose collectors are respectively connected to the other terminals of the visible indicators 68 and 70 through the connector 58.

The voltage imposed upon the positive terminal of the differential amplifier 112 is less than the voltage imposed upon the negative terminal of the differential amplifier 114. Therefore, by proper choice of the coil 102 to produce a desired voltage output from the differential amplifier 108, the output of the differential amplifier 112 can be always negative, while the output from the differential amplifier 114 can be positive or negative depending on the relative voltage by the differential amplifier 108. As a result, the transistor 130 can be caused to conduct at all times while the transistor 132 conducts only when a sufficiently negative output is produced by the differential amplifier 114. As a result, the visible indicator 68 is illuminated by electrical current passing through the transistor 130 at all times that the on-off switch 66 has caused the relay switch 82 to be in its closed position. Accordingly, the visible indicator 68 serves as a indication that the high voltage is being applied to the head 30 of the hand tool 12.

On the other hand, since the transistor 132 conducts only when a voltage of sufficient magnitude is produced by the differential amplifier 108, visible indicator 70 will only be illuminated when sufficient current passes through the lead 104 from the ground clamp 62. This, of course, indicates that the conducting surfaces 46 and 46' have detected a break in the integrity of the dielectric coating 18 on the elongated member 16.

While the foregoing is a detailed description of a preferred embodiment of the present invention, those skilled in the art will understand that various modifications can be made to the above-described embodiment without departing from the spirit of the invention. In particular, it will be understood that the conducting surfaces 46 and 46' can alternatively be made from a conducting foam, a thin copper sheet, or a metal braid, as long as their combination with the spongy inserts 40 and 42 cause the conducting surfaces 46 and 46' to conform to the outer surface 20 of the elongated member 16. In this way, the conducting surfaces 46 and 46' simultaneously contact a substantially complete circumference or perimeter of the elongated member 16, allowing virtually entirely all of the dielectric coating 18 to be tested in one pass of the hand tool 12 along the elongated member 16. Therefore, the spirit and scope of the present invention are to be limited only by the following claims.

We claim:

1. Apparatus for testing the integrity of a dielectric coating on an outer surface of an elongated electrically conductive member, the outer surface having a perimeter around the elongated member, comprising:
    two opposed conducting surfaces adapted to form an electrically conductive path on the dielectric coating;
    a split ring that supports said conducting surfaces and is adapted to force said conducting surfaces to form the electrically conductive path continuously contacting the dielectric coating along a closed curve around the perimeter of the outer surface;
    a ground connector adapted to make an electrical connection to the elongated member;
    a cable adapted to make an electrical connection to said two opposed conducting surfaces; and
    an electrical circuit connected between said cable and said ground connector for imposing a high voltage between said cable and said ground connector for detecting passage of electrical current through the dielectric coating in response to said high voltage, and for producing said first indication signal.

2. The apparatus of claim 1, wherein said circuit means comprises a source of a high voltage connected between said ground connector and said cable.

3. The apparatus of claim 1 wherein said ground connector further comprises a switch for interrupting the electrical connection to the elongated member.

4. The apparatus of claim 1 wherein each of said two opposed conducting surfaces comprises a conductive spongy material that can conform to the outer surface of the elongated member.

5. The apparatus of claim 4 wherein said conductive spongy material comprises a thin conductive sheet.

6. The apparatus of claim 4 wherein said conductive spongy material comprises a metal braid.

7. The apparatus of claim 4 wherein said conductive spongy material comprises a conducting foam.

8. The apparatus of claim 1, further comprising a handle attached to said split ring and adapted to move the apparatus along the elongated member.

* * * * *